US012070328B2

(12) United States Patent
Ostrow

(10) Patent No.: US 12,070,328 B2
(45) Date of Patent: Aug. 27, 2024

(54) WEARABLE PERSONAL HEALTHCARE SENSOR APPARATUS

(71) Applicant: Alvin Ostrow, Atlanta, GA (US)

(72) Inventor: Alvin Ostrow, Atlanta, GA (US)

(73) Assignee: Alvin Ostrow, Atlanta, GA (US)

( * ) Notice: Subject to any disclaimer, the term of this patent is extended or adjusted under 35 U.S.C. 154(b) by 731 days.

(21) Appl. No.: 17/055,201

(22) PCT Filed: May 14, 2019

(86) PCT No.: PCT/US2019/032268
§ 371 (c)(1),
(2) Date: Nov. 13, 2020

(87) PCT Pub. No.: WO2019/222250
PCT Pub. Date: Nov. 21, 2019

(65) Prior Publication Data
US 2021/0219909 A1     Jul. 22, 2021

Related U.S. Application Data

(60) Provisional application No. 62/670,902, filed on May 14, 2018.

(51) Int. Cl.
| | |
|---|---|
| *A61B 5/00* | (2006.01) |
| *A61B 5/0205* | (2006.01) |
| *A61B 5/021* | (2006.01) |
| *A61N 1/39* | (2006.01) |
| *G16H 20/17* | (2018.01) |
| *G16H 40/20* | (2018.01) |
| *G16H 40/67* | (2018.01) |
| *G16H 50/30* | (2018.01) |

(Continued)

(52) U.S. Cl.
CPC .......... *A61B 5/4839* (2013.01); *A61B 5/0022* (2013.01); *A61B 5/0024* (2013.01); *A61B 5/0205* (2013.01); *A61B 5/021* (2013.01); *A61B 5/747* (2013.01); *A61N 1/3904* (2017.08); *G16H 20/17* (2018.01); *G16H 40/20* (2018.01); *G16H 40/67* (2018.01); *G16H 50/30* (2018.01); *H04W 4/90* (2018.02); *A61B 5/02438* (2013.01); *A61B 5/1112* (2013.01); *A61B 5/6804* (2013.01)

(58) Field of Classification Search
None
See application file for complete search history.

(56) References Cited

U.S. PATENT DOCUMENTS 3,985,133 A * 10/1976 Jenkins ................ A61M 5/172
                                                                           604/152
6,628,989 B1   9/2003 Penner et al.
(Continued)

OTHER PUBLICATIONS

International Search Report for application PCT/US19/32268 with mailing date Oct. 7, 2019.

*Primary Examiner* — Manuel A Mendez
(74) *Attorney, Agent, or Firm* — Parker Poe Adams & Bernstein, LLP; Paul E. Dietze

(57) ABSTRACT

A medical system worn by an individual comprising in certain embodiments a central processing unit, a memory unit containing programming and diagnostic values, a global positioning system unit, a wireless communications component, at least one physiologic sensor, and at least one medicament administration device containing at least one active pharmaceutical ingredient.

19 Claims, 5 Drawing Sheets

(51) Int. Cl.
*H04W 4/90* (2018.01)
*A61B 5/024* (2006.01)
*A61B 5/11* (2006.01)

(56) References Cited

U.S. PATENT DOCUMENTS

| | | | |
|---|---|---|---|
| 2001/0056227 A1* | 12/2001 | Gopinathan | A61B 5/6806 |
| | | | 128/903 |
| 2005/0148882 A1 | 7/2005 | Banet et al. | |
| 2009/0299156 A1 | 12/2009 | Simpson et al. | |
| 2017/0235917 A1* | 8/2017 | Bighamian | G16H 40/67 |
| | | | 705/2 |
| 2017/0281065 A1 | 10/2017 | Newberry | |
| 2017/0347894 A1* | 12/2017 | Bhushan | A61B 5/14542 |

* cited by examiner

WEARABLE PERSONAL HEALTHCARE SENSOR APPARATUS

This application claims the benefit of U.S. Provisional Application No. 62/670,902 filed May 14, 2018, which is hereby incorporated by reference.

BACKGROUND

The trend of chronic disease of prevalence and mortality in the USA over the last ten years surround cardiovascular disease, cancer, chronic lung disease, diabetes and arthritis. The 21st century areas of chronic diseases are mostly involved in non-communicable diseases mostly attributed to lifestyle and living in modern urban cities. Herein, we will use the term NCD (chronic disease—non-communicable). The United States National Center for Health Statistics defines a 'Chronic condition as one of three months in duration.' The general definition of an NCD is a disease that has a prolonged course, that does not resolve spontaneously, and to which a complete cure is rarely achieved. The characteristics of NCDs are chronic illnesses, non-communicable degenerate diseases characterized by uncertain etiology with multiple risk factors, long latency, prolonged course of illness, non-contagious origin that can lead to functional impairment or disability. There are risk factors that are involved in NCD, such as personal behaviors or lifestyle, an environmental exposure, or hereditary characteristics that are associated with an increase of an occurrence within a particular disease.

According to the Centers for Disease Control (CDC), blood pressure is the force of blood pushing against the walls of your arteries, which carry blood from your heart to other parts of your body. Blood pressure normally rises and falls throughout the day. But if it stays high for a long time, it can damage your heart and lead to health problems. High blood pressure (also known as Hypertension) raises your risk for heart disease and stroke, which are leading causes of death in the United States. High blood pressure has no warning signs or symptoms, and many people do not know they have it. The only way for an individual, or an individual's caretakers, to know if that person has high blood pressure is to measure it. Then, steps may be taken to control it if it is too high. High blood pressure is called the "silent killer" because it often has no warning signs or symptoms, and many people do not know they have it. Measuring blood pressure requires a significant step of visiting a clinic or drug store, or properly operating a complicated medical device at home.

Consequently, there is a need in the art for a simpler and more passive means of measuring blood pressure and reporting the results.

SUMMARY

The following presents a simplified summary of the invention in order to provide a basic understanding of some aspects of the invention. This summary is not an extensive overview of the invention and is not intended to be limiting in scope nor exhaustive in breath. It is not intended to identify key or critical elements of the invention or to delineate the scope of the invention; its sole purpose is to present concepts of the invention in a simplified form as a prelude to the more detailed description that is subsequently presented.

A medical device worn by an individual previously diagnosed with a blood pressure condition comprising a central processing unit, a memory unit containing programming and diagnostic values, a wireless communications component, at least one sensor capable of measuring diastolic and systolic blood pressure, at least one sensor capable of measuring heartrate, and at least one medicament administration device containing at least one active pharmaceutical ingredient; wherein the central processing unit, the memory unit, and the wireless communications unit are inside a single container removably affixed to a patient; wherein the central processing unit receives information from, and sends information and instructions to, the memory unit, and wireless communications unit, the sensors, and the at least one medicament administration device; wherein the central processing unit may instruct the at least one medicament administration device to administer at least one active pharmaceutical ingredient to a patient; wherein the wireless communications component is in frequent communication with remote computers on a propriety healthcare provider network via at least one internet access point; and, wherein the frequent communication(s) contains information about sensor measurements, and central processing unit instructions.

A medical device wherein the single container is removably affixed to the patient's body and further comprises an automatic external defibrillator. A medical device wherein the wireless communications component connects to the Internet through either at least one cellular communications tower or at least one Wi-Fi access point. A medical device wherein the central processing unit receives information from, and sends information and instructions to, the sensors by Bluetooth wireless technology. A medical device having at least two sensors capable of measuring diastolic and systolic blood pressure removably affixed to the patient's body. A medical device wherein one blood pressure sensor is removably affixed to one of the patient's arms, and one blood pressure sensor is removably affixed to one of the patient's ankles. A medical device further comprising a global positioning system located inside the container, and which provides location information to the central processing unit. A medical device wherein the at least one active pharmaceutical ingredient is one that is approved by and indicated by the FDA to reduce blood pressure in patients, and wherein the at least one medicament administration device is a transdermal patch. A medical device wherein the at least one active pharmaceutical ingredient is classified as a beta blocker. A medical device wherein the at least one active pharmaceutical ingredient is classified as a central-acting agent. A medical device wherein the at least one active pharmaceutical ingredient is classified as a vasodilator.

A medical device further comprising two sensors capable of measuring diastolic and systolic blood pressure wherein: there is only one medicament administration device that is a transdermal patch removably affixed to the patient's skin under a garment; there is only one active pharmaceutical ingredient that is clonidine; the central processing unit may instruct the medicament administration device to administer clonidine based on the two blood pressure sensor measurements, and the at least one heartrate sensor measurement. A medical device of claim wherein the central processing unit instructions, the blood pressure sensors and heartrate sensor(s) measurements, and the administration of clonidine comprise a closed feedback control loop further comprising an emergency routine exit point to the loop.

A method for monitoring a patient's blood pressure and administering a drug in a closed feedback control loop comprising: a central processing unit receiving wireless information about blood pressure from at least one blood pressure sensor that is removably affixed to a patient's body, and receiving wireless information about heartrate from at least one heartrate sensor that is removably affixed to a patient's body; processing the received information in a central processing unit; determining whether an emergency condition exists by comparing the processed information to pre-programmed values in the central processing unit; if there is an emergency condition, activating an emergency routine requiring wirelessly communicating with a health-care provider; if there is no emergency condition, determining whether to administer a drug based on an administration evaluation program in the central processing unit; if a drug is determined to be administered, determining a dosage of the drug and from which application device to administer it, and sending a set of instructions containing dosage information to a medicament application device located on or near the patient's body. A method wherein the emergency routine comprises communicating with a pre-determined health care provider, communicating with a city or county emergency service provider, and communicating with at least one family member's mobile telephone via text message and pre-recorded voice call. A method wherein the emergency routine further comprises communicating blood pressure and heartrate sensor information in real time with emergency service providers over the Internet. A method wherein the central processing unit is sending the set of instructions via a wired system to the medicament application device, and wherein the medicament application device is programmed to confirm the fidelity of the set of instructions. A method wherein the drug is an FDA approved drug indicated for hypertension and is selected from the class of beta blockers, central-acting agents, and vasodilators.

A medical system worn by an individual comprising a central processing unit, a memory unit containing programming and diagnostic values, a global positioning system unit, a wireless communications component, at least one sensor capable of measuring diastolic and systolic blood pressure, at least one sensor capable of measuring blood sugar, at least one sensor capable of measuring heartrate, at least one sensor capable of measuring an active pharmaceutical ingredient in the blood, and at least one medicament administration device containing at least one active pharmaceutical ingredient; wherein the central processing unit, the memory unit, the global positioning system unit, and the wireless communications unit are inside a single container removably affixed to a patient; wherein the central processing unit receives information from, and sends information and instructions to, the memory unit, and wireless communications unit, the sensors, and the at least one medicament administration device in a closed feedback control loop further having an emergency routine exit in the loop; wherein the wireless communications component is in constant communication with remote computers on a propriety healthcare provider network via at least one internet access point; wherein the frequent communication(s) contains information about sensor measurements, location information from the global positioning system unit, and central processing unit instructions; wherein the central processing unit may instruct the at least one medicament administration device to administer to a patient one or more active pharmaceutical ingredient(s), such as beta blockers, central-acting agents, vasodilators, alpha blockers, alpha-beta blockers, aldosterone antagonists, and renin inhibitors, and/or substances FDA approved for the treatment of insulin.

Further features of the present invention will be apparent from the description that follows. After review, such features may, in part, be obvious from the description or may be learned by practice of the invention. It is to be understood that both the foregoing general description and the following detailed description are exemplary and explanatory only and are not restrictive of the invention, as claimed.

DETAILED DESCRIPTION OF FIGURES AND EMBODIMENTS

Having generally summarized the invention disclosure above, a further understanding can be obtained by reference to certain specific examples illustrated below which are provided for purposes of illustration only and are not intended to be all inclusive or limiting unless otherwise specified. Accordingly, term or phrases such as "for example" or "e.g." and the like, even if they are not coupled with a modifier such as "without limitation" or the like, are not intended to be limiting of the disclosure of the invention.

Reference now will be made in detail to embodiments and examples of the present invention. The particular components and amounts thereof recited in these examples, as well as other conditions and details, should not be construed to unduly limit this invention.

Figure 1:
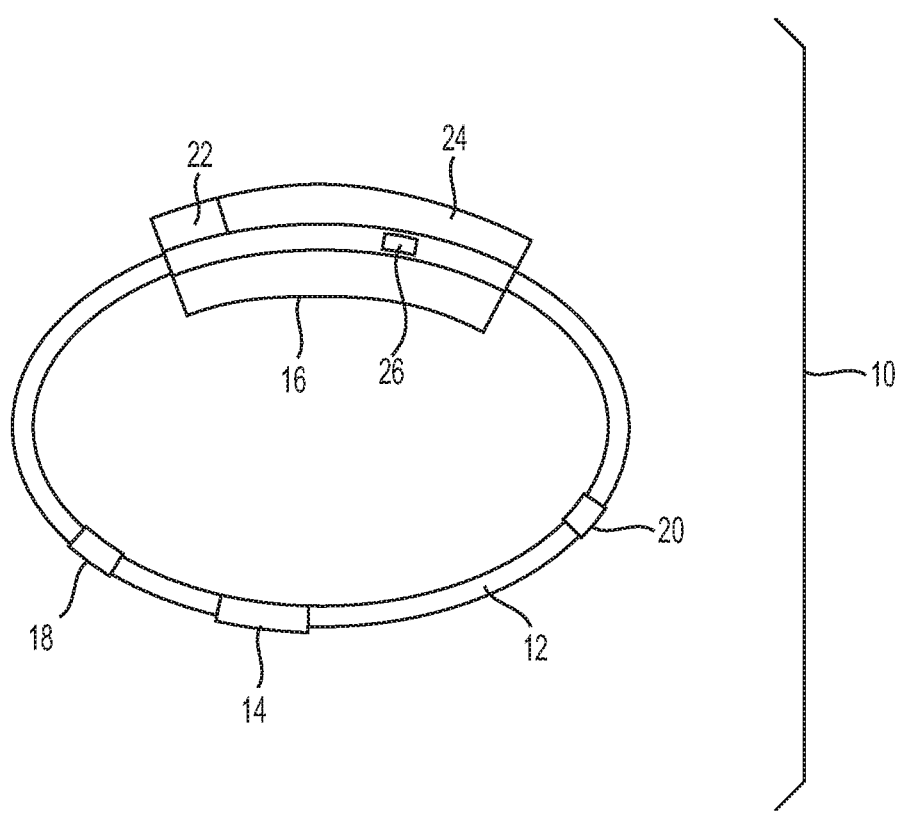
FIG. 1 illustrates an embodiment of the invention as a wearable personal sensor device affixed with a strap.

FIG. 1 illustrates an embodiment of a personal healthcare sensor apparatus 10. This paragraph presents a general overview of the functionality of the device and examples of usage. However, it is understood that this overview is non-limiting and that further embodiments and features of the device 10 and invention are explained in more detail herein. Generally, the device 10 is worn by a person who expects or wishes to more passively measure his or her blood pressure or other bodily characteristic identifiable by a sensor. In other embodiments, the device may be implanted under or on the skin, or attached to the body through a separate implanted device. The device 10 contains at least one sensor 16 that measures physiological characteristics. Certain types of sensors may include those that detect bodily fluids and chemical components thereof. For example, a certain sensor may detect blood sugar, or may detect chemicals including active pharmaceutical ingredients or drugs in the blood, saliva or other bodily fluids, and the blood concentration thereof. Other sensors may be able to detect paramagnetic drugs and concentration based on a comparison between hemoglobin magnetic qualities and drug magnetic qualities. Optional additional sensors 18, 20 are shown in FIG. 1. The device 10 is typically worn or affixed to a person's body directly or indirectly, e.g., through an article of clothing or on the skin. Typically the device 10 is affixed with a strap 12 and further configured for optimal sensor readings by using a buckle 14. For certain sensors, a tight fit around an appendage or close to a blood vein or vessel is preferred which the buckle 14 may help to accomplish. The sensors 16, 18, 20 may perform a similar function as to each other, or may sense different bodily or health characteristics. Additionally, although not pictured in FIG. 1, there may be more than three sensors, and typical embodiments may have up to 20-30 sensors. The device 10 converts sensor 16 measurements into data, processes the measurements through a computing module (not shown in FIG. 1), analyzes the data including by comparing the data to preset values, and then determines based on such comparison the likelihood of whether such sensor readings are normal. The device 10 then sends its conclusions about the existence or likelihood of a normal or abnormal health reading to a proprietary computer based remotely. Sometimes in addition to sending the device's 10 locally determined conclusions about health information, the device 10 also sends raw sensor data, and/or pre-processed sensor data as well. The device 10 also sends with its communication certain data about the current time, location, device identification, and location information. This information may be transmitted via an antenna 26. A remote proprietary computer operated by healthcare professional may receive the signal about the health characteristics from the device 10 and may be programmed to immediately least an emergency administrator/dispatch through a variety of means including voice call, text, page, email, siren, room or building light changes or any combination thereof. Such contact with at least an administrator will typically include information sufficient for anyone contacted to respond to the emergency situation by providing assistance.

Further examples, details and embodiments follow further below, and set forth in this paragraph is a general example embodiment of the invention and its functionalities. An elderly person wearing a device 10 on his upper arm may be going on a routine walk in the morning. The person's body may begin to experience an abnormal blood pressure, either high or low. The device 10 will immediately detect changes in the blood pressure via at least one or more of the optional sensors 16, 18, 20. The device 10 may also have a sensor to detect heartrate, or such a heartrate sensor may be one of the optional sensors 18, 20. The device 10 analyzes all sensor data, compares it to pre-programmed values indicating "normal" and "non-normal" sensor data, and determines whether there is a high likelihood of an adverse health situation. Typically, information that is analyzed includes at least systolic blood pressure, diastolic blood pressure, and heartrate. After the data analysis indicates the presence of an adverse health situation within a certain confidence interval that may be determined by the number of sensors that may be in a non-normal range, the device 10 then utilizes its antenna 26 to signal computers operated by at least a family member, a health care provider, or emergency professionals. Based on the information received from the device 10, a family member, health care provider, or emergency professionals can quickly or immediately act, interactively or onsite, to help or assist the person experiencing the adverse health situation.

A typical device 10 will contain an antenna 26 or other wireless transmission device. The antenna 26 permits the device to communicate, either constantly with periodicity, or upon certain conditions, with other remotely located devices. In one embodiment, the antenna 26 utilizes cellular technology such as 2G, 3G, 4G, 5G and/or LTE to communicate with a commercial wireless provider to transmit and receive information. Because of the wide availability of the commercial cellular service this permits the device 10 to generally communicate via antenna 26 with other devices from anywhere such cellular service or backup service is available. In other embodiments, the antenna 26 may contain transmission technology such as Bluetooth, Z-wave, Wi-Fi 802.11 b/g/n/ac, and antenna technology to permit communications through frequencies utilized by government agencies, military, law enforcement agencies, emergency, and/or public service networks. In certain embodiments wireless technology (in particular but without limitation Bluetooth, Z-wave, and Wi-Fi) permit one device 10 to communicate with other devices 10 either worn by the same user, affixed to non-users, or to devices 10 in the same general geographic vicinity.

A typical device 10 will also contain at least one, and typically a plurality of sensors 16, 18, 20. As discussed further, a collection of different sensors 16, 18, 20 are available for usage in the device 10. Certain sensors may be selected by a user or a purchaser to maximize the usage of the device 10. Broadly, sensors may be selected for measuring different types of human physiology or physiological responses or phenomena. The sensors 16, 18, 20 in a device 10 include without limitation at least one, and with the option of having a plurality of any of the following instruments: heart rate monitor, blood oxygen level monitor, blood pressure monitor, electrodermal activity (and other somatic markers known in the art such as measurements of the sympathetic nervous system), sweat (including rate of sweat), body chemicals (e.g., such as cortisol or hormones). Other instruments commonly known to those in the art would also be understood to be included as sensors in the device 10. Typically, sensors 16, 18, 20 would be understood to be selected based on the likelihood of their detecting indicia of blood pressure. However, depending on the unique attributes of an individual body or blood pressure response, the sensor 16, 18, 20 selection could vary significantly. Additionally, sensor selection could vary based on budget, in particular when a plurality of devices 10 are being purchased at a time such as in bulk by a healthcare providers, insurance company, institution or elderly or other care provider. Certain embodiments of the invention may include all of the sensors expressly listed above and more although typical embodiments would not. Typically, the device 10 would be waterproof or water resistant.

It would be understood by one in the art that there may be reasons why a plurality of the same type of sensor 16, 18, 20 may be selected include: having redundant sensors in case of failure, having additional sensors 16, 18, 20 to monitor measurement deviation over time to flag tuning or maintenance, or to capture different aspects of the measured phenomena such as a different ranges, or multiple readings that can be compared, or simply different aspects of the same phenomena. For example, multiple blood pressure sensors designed using an automated appendage cuff may be used to take multiple readings of blood pressure from different appendages or body locations.

A typical device 10 may contain a screen or touch screen 24. Such a screen 24 permits interaction with the device 10 and with its internal components for maintenance, setup, diagnostics, control, or information output in a human understandable or readable format. The screen 24 typically also includes a display that may provide passive information about the environment such as time and weather, and may provide reminders for important event or notifications, e.g., medication reminders. The screen 24 display further may be able to be controlled by a completely independent device such as a phone so that it could display text messages or other information from the phone. Other features known in the art for a display on a wearable device are also contemplated. Typically, the screen 24 would include at least one button that a user or other person in a health emergency or potentially medically adverse situation could rely on to transmit an emergency signal to others. Additionally, the emergency button 22 on the device is an easily located area on the apparatus 10 permitting a user to press it in the event of a healthcare or blood pressure related emergency. Typically, the physical emergency button 22 would have the same effect on the apparatus 10 as the screen 24 emergency button would have, i.e., contacting emergency services or family member(s). In certain embodiments, the button 22 may be programmed or physically installed to only respond in the event it is held for a certain time period, or pressed in a certain pattern, which depending on the individual using it would be optimal. For example, if a blood pressure emergency or sensation is felt, then in many cases the individual wearing the apparatus 10 would be physically able to press and hold the button for 5 seconds, 10 seconds, or even up to 20 seconds. In particular, if the person using the apparatus 10 is not capable or comfortable with electronic devices, then a certain pattern may be preferable, such as pressed for around 0.25 to 1 second, un-pressed for 0.25 to 1 second, and then pressed again for around 0.25 to 1 second. This would reduce the amount of false positives because intentional pressing is required, while still ensuring that an emergency signal is sent quickly. Depending on the preferences of the individual wearing the apparatus and the family or providers, the emergency button may simply be used a reliable means of signaling and may not be used for emergency purposes at all. For example, the signal if pressed in a particular on-off-on pattern, or on-off-on-off-on pattern could indicate that the individual is ready for pickup or a ride, or needs help taking routine medication. In further embodiments of the invention, the emergency button is a panic button and is configured to directly communicate with emergency management services to report an emergency. In one embodiment, the panic button would directly communicate to a 911 service such as a PSTN network over a cellular phone network, and in other embodiments, the panic button would communicate over a VOIP protocol 911 service. In still other embodiments, an emergency button or a panic button may be configured to call for a ride share service such as Uber or Lyft or a taxi for transportation to an emergency room or health care provider if an ambulance is unavailable.

In a further embodiment of the device 10 of FIG. 1, the device 10 may have hardware and/or software installed providing diagnostic functionality such that in the event the device 10 malfunctions, it will provide an indicator, noise, or light. The screen 24 may be utilized in certain embodiments to provide a display alert, and in still other embodiments an audio speaker may be installed to provide audible alerts. In other embodiments, the alerts about a malfunction may be transmitted to health care providers. Thus, the device 10 would have improved safety as it may provide such alerts regarding malfunction to both patients and physicians.

Although not expressly shown in FIG. 1, the internal components of the device 10 are all expected to be connected to each other through two-way data transmission channels (such data connection includes to the battery which may have an attached sensor to provide data about its status, charge, voltage or current output or input) although it is noted some non-power data transmissions channels may be wireless or transmitted via radio. It is also contemplated that a typical embodiment of the instant invention will employ off the shelf technologies available for monitoring blood pressure, pulse, heart rate, respiration, and/or electrocardiogramaugh not shown in FIG. 1, for patients at risk of heart attack, an automated external defibrillator ("AED") may be incorporated as a component in the device 10. The AED may be activated should an infarct or heart failure be detected, e.g., by a sensor. A flowchart and feedback loop is discussed later in the specification wherein the device 10 may determine whether to active such an AED device under appropriate circumstances.

The device 10 is contemplated to be used for treatment and management of a medical condition or disorder, and also for general health and wellness. Regarding the latter use, patients suffering from, or individuals who consider that they may be at risk for certain conditions, may employ the device 10 to monitor their health. For example, if an individual is presently healthy, but wishes to passively monitor his or her blood pressure, the device 10 may be configured and programmed to achieve that, i.e., without administration of any drug, and even without any monitoring by health care professionals. In other examples and embodiments of the device 10, other sensors could be used to monitor other physiological characteristics of an individual's body. Accordingly, a suite of sensors is contemplated that may be configured by an individual to achieve his or her own wellness or general health goals based on actual or perceived risks, or simply to collect data about the individual's own body, e.g., to watch for patterns or determine how that person's own body operates in certain conditions or over time. Further embodiments may allow the patient and health care provider to coordinate or conduct rehabilitation or physical wellness programs interactively, including communicating dietary regimens, stress reduction, mindfulness, and/or biofeedback.

Figure 2:
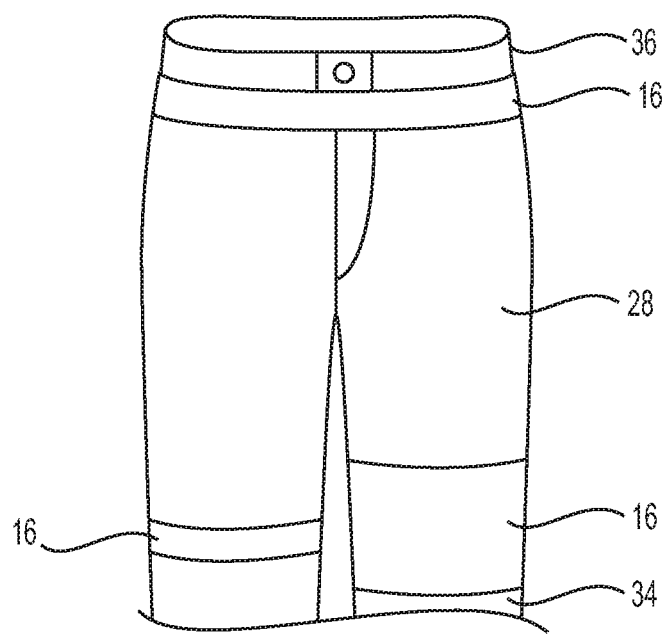
FIG. 2 illustrates an overview of an embodiment of the invention having certain sensors placed upon a garment.

FIG. 2 illustrates an embodiment of a clothing wearable personal healthcare sensor apparatus on a garment 28 that is a pair of pants. The screen in this embodiment is not shown but would typically be worn on a wrist of the user or carried in a pocket and would be understood to display at least time as well as basic instrument readouts. The sensors 16 in this embodiment are located at areas of the body that may be used for detecting blood pressure and heartrate. For example, two sensors 16 have been selected for this embodiment with one near the ankle, and one covering the shin of the individual up to the knee. An additional sensor 16 has been selected for near or about the waist of the individual, although it may be placed higher or lower as needed for the most reliable blood pressure and/or heart rate reading. The waist portion 36 of the garment 28 and the leg portion 34 of the garment may each be integrated with a sensor 16, e.g., sewn into the garment 28, or affixed by other means such as fabric glue or safety pins. Certain sensors may require skin contact and thus any affixation would preserve such contact. In particular, certain sensors may determine the dosage of the drug in the device 10 as it transverses through the stratum corneum, which may be significant in relation to how much drug concentration is within the bloodstream particularly for transdermal administration as part of a feedback loop. Other sensors may not require skin contact and so could have a layer of comfortable fabric or other material in between the sensor and the skin, or the rest of the garment 28. Other non-limiting examples of affixation, or linking of the apparatus 10 to an individual may include, but are not limited to, mechanical affixing other than a strap, magnetic affixation, buttons, and also physical placement or affixation near the individual or on or affixed to a physical object with which the individual is typically nearby or moves with.

Typically, the embodied device 10 of FIG. 2 is worn by a patient or individual in need to blood pressure monitoring including those concerned about their own health. It is contemplated that the sensors 16 or apparatuses generally may communicate with other devices connected to the same user through antennae to share at least device component functionality such as without limitation information from sensors 16, or even computing module processing power or data storage. In one embodiment, an individual wears one apparatus 10 on a particular garment 28 and a separate apparatus may be connected to or inside of the individual's other garment that may be removed frequently such as a coat or sweater. The devices communicate with each other to share data and other information, including the location of the devices 10 relative to each other. If the apparatuses 10 determine that they are apart, or that they are separated in some fashion and one or more sensor or apparatus is no longer connected to a body, e.g., based on evidence of blood pressure measurements from some sensors but not others, then the device can adjust is measurements and calculations for determining the presence of an adverse health event.

Figure 3:
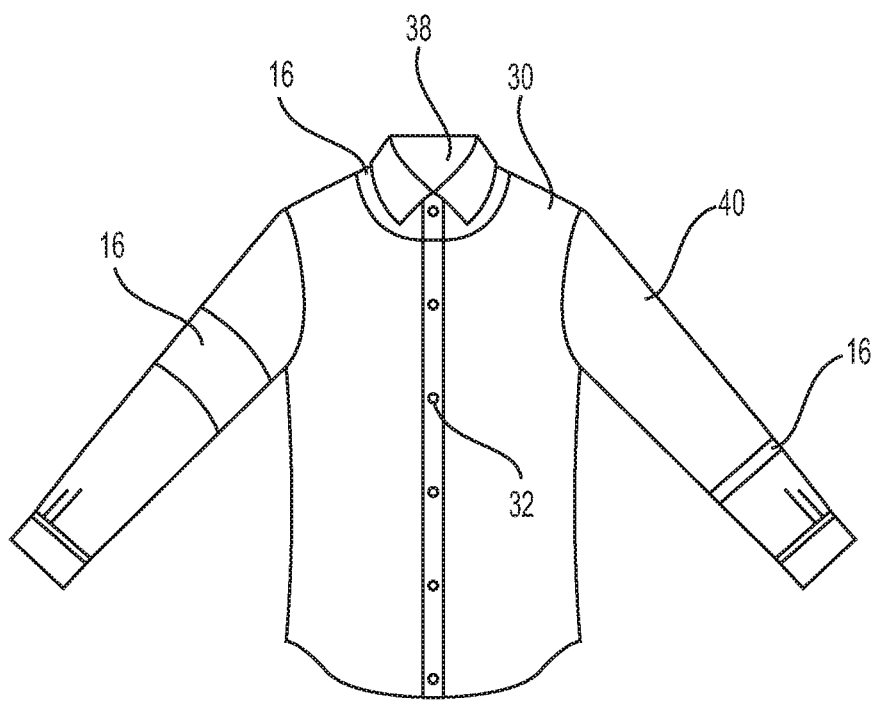
FIG. 3 illustrates an overview of an embodiment of the invention having certain sensors placed upon a garment.

FIG. 3 is similar to FIG. 2 and shows an embodiment of a garment 30 in this case worn by an individual as a shirt, coat, sweater. A sensor 16 is depicted below the elbow on the individual's left handed sleeve 40. A sensor 16 is additionally depicted on or near the collar 38 or neck area of the garment 30. Additionally, a sensor 16 is depicted near the elbow on the individual's right sleeve 40 with a broader sensing width or area than the sensor on the individual's left sleeve. Typically, at least one or more of the sensors would measure blood pressure but as discussed elsewhere in the specification other measurements may also be taken by the sensors depending on design, expected usage, cost, and implementation. As with the sensors in FIG. 2, the sensors in FIG. 3 may be sewn in or otherwise affixed to the garment 30 or to portions of the garment such as the collar 38, or either sleeve 40. The sensors may or may not touch the skin depending on the usage. Buttons 32 are optional depending on the garment. In certain embodiments, one or more buttons 32 may overlap with the sensor and so may be integrated into the function of a sensor 16 or accompanying apparatus 10. For example, the fastening of a button sewn into an apparatus 10 and/or sensor 16 may be detected and may satisfy a condition required prior to the recording of blood pressure or heartrate.

Figure 4:
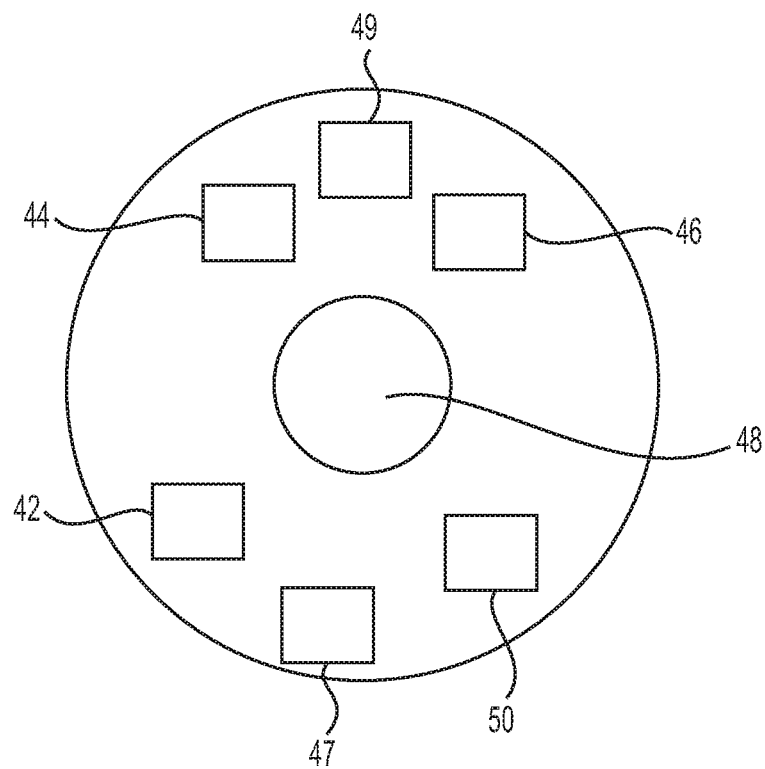
FIG. 4 illustrates an overview of an embodiment of the invention having certain functional modules for typical operation.

FIG. 4 is a depiction of an embodiment of the device 10. The device here may be held as a standalone device and may wirelessly connect to one or more sensors placed elsewhere which each may have their own separate power supply or may be connected to the embodiment of FIG. 4. Additionally, the device 10 may wirelessly connect to other similar devices 10 placed elsewhere.

A typical device 10 will also contain at least one battery 50. A battery 50 provides power to the device 10 and its components. Multiple batteries may be expected to be used to provide backup power to the device 10, or to provide additional power for when multiple sensors (either sensors 49 on the device 10 or on other devices, or standalone) or other components are operating at the same time. Typically, the battery 50 would be a commercially available rechargeable type of battery relying on an alkali metal such as lithium. However, other batteries 50 known in the art are contemplated including without limitation those relying on nickel, cadmium, lead, zinc, or aluminum.

A typical device 10 will also contain a computing module 42. Broadly, the computing module operates as a standalone programmable mini-computer and/or microcontroller. Accordingly, the computing module 42 will typically contain at least one processing unit, including but not limited to a central processing unit or CPU, working memory storage, and also may contain long-term data storage unit. The computing module 42 is typically connected to all of the other components, including, without limitation, a sensor 49, battery 50, and GPS unit 47 through at least one two-way physical data transmission channel (now shown in the figure). Through the data connections, the computing module would be expected to receive data input from the components on either a continual basis a periodic basis, or subject to certain conditions. Additionally, the computing module would be expected to transmit data to the components either on a continual basis, a periodic basis, or subject to certain conditions. As one example of an operational embodiment, the sensor 49 on the device 10 transmits data to the computing device 42 which processes the data and transmits it to the antenna 46 or external communications module for subsequent external transmission.

A typical device 10 may contain a data and memory module 44 separate from any memory or data component that may be present in the computing module 42. The data module 44 is connected to at least the sensor 49 and computing module 42 by data channels (not shown) and can serve as extra short-term memory or medium or longer term data storage for the computing module 42 or sensor 49. Additionally, the data module 44 and data channel connections are all sized in terms of total data capacity, write speed, and read speed to permit the regular and periodic capture of blood pressure readings taking into consideration the sensor 49, the computing module 42, and any other connected or wirelessly transmitted sensor or apparatuses.

The GPS device 47 depicted in the embodiment in FIG. 4 is understood to be configured to receive signaling and determine location information from the GPS satellite system. However, the device 47 may also incorporate ground-based location positioning technology such as through cellular towers.

In certain embodiments of the invention, the device 10 of FIG. 4 may be physically or wirelessly connected to one or more transdermal medical application devices (not shown). Such devices are known in the art and operate to release a formulation, drug product, prodrug, or active pharmaceutical ingredient onto a patient or individual's skin. In the embodiments contemplated herein, the release mechanism is usually electrically based (in particular iontophoretic transdermal drug delivery systems) but other conventional release mechanisms or administrations are also contemplated. In one example of the operation of the invention, one or more sensors would provide input by wired connections or wirelessly through the communications module 46 and would be processed by a CPU 42. The CPU 42 would process the sensor readings based on at least the type of physiological measurement being made (e.g., blood pressure, heartrate), source of measurement on the body (e.g., waist, chest, left arm, or right leg), the signal quality, and comparisons from preset programmed values. Based on the processing and comparisons, the CPU 42 would signal a result to the communications module 46 for external transmission and/or would conduct further processing to determine whether to signal one or more transdermal patches for medicament application. Depending on the type of result indicated by the CPU 42, the communications module 46 transmission could be configured in machine or human readable format (or both) and routed to a cell phone, e-mail address, fax, health care provider, triage or urgent care provider, emergency operator, or 911 emergency service. Or, in certain cases such as for regular results or measurements, the transmission would be routed to routine storage either on the device or offsite on a remote computer. As an example, an abnormal blood pressure readout would typically be routed in human and machine readable format to a healthcare provider and a family member cell phone would receive a text alert as well with a status. For such abnormal results, the CPU 42 would conduct another set of computations for whether to administer a transdermal medication. Such computations would be based on preset values and programmable language vetted and configured by healthcare professionals supporting the individual wearing the device. Depending on the type of abnormal readout, e.g., which may or may not take into account high and/or low systolic and/or diastolic blood pressure, heartrate, sweat rate or composition, body temperature, environmental temperature, and/or other information, the CPU 42 would signal one or more transdermal patches for medicament application.

A typical transdermal application would involve an individual who is wearing a patch having a medicament used for treating high blood pressure of other hypertensive disorder. The particular medicament for the transdermal would usually be clonidine, or a beta blocker. In certain circumstances, the CPU 42 may only signal to effect or cause a transdermal application based on either one set or a plurality of sets of collected data and/or a certain time period. Whether a certain number of data points or a certain time period must be reached prior to signaling for application for the transdermal patch may depend on the approved indications or specific provider prescriptions for using such administered medicaments. For example, in certain cases a doctor may prescribe a once weekly administration in a transdermal patch if the individual has certain risk factors (or absence of the same), or if blood pressure was recorded previously within a certain threshold. In still other cases, a provider, or the patient or individual him or herself, may prescribe or prefer a period of administration of 24 hours, or less. An optional feature of the device is to employ a control system to monitor and manage administration of the API. In such a configuration, the device will monitor sensor readings and based on programming and preset values selected by the individual wearing the device or a provider, the device would interpret the sensor data, determine whether to administer medicament through a transdermal patch or other medical device (including an insulin pump for certain diabetic patients). In a manual configuration of the device, there would be no automated administration based off of sensor input, however administration may be made based off of the time of day, a timer, or an active decision or selection made by the individual wearing the device or a provider. It is noted that certain embodiments are expected to be operated in the manual configuration where such decisions or selections about administration are made from a personal electronic device (such as a smartphone) or a computer connected to the Internet, local network, or local channel such as Bluetooth.

Figure 5:
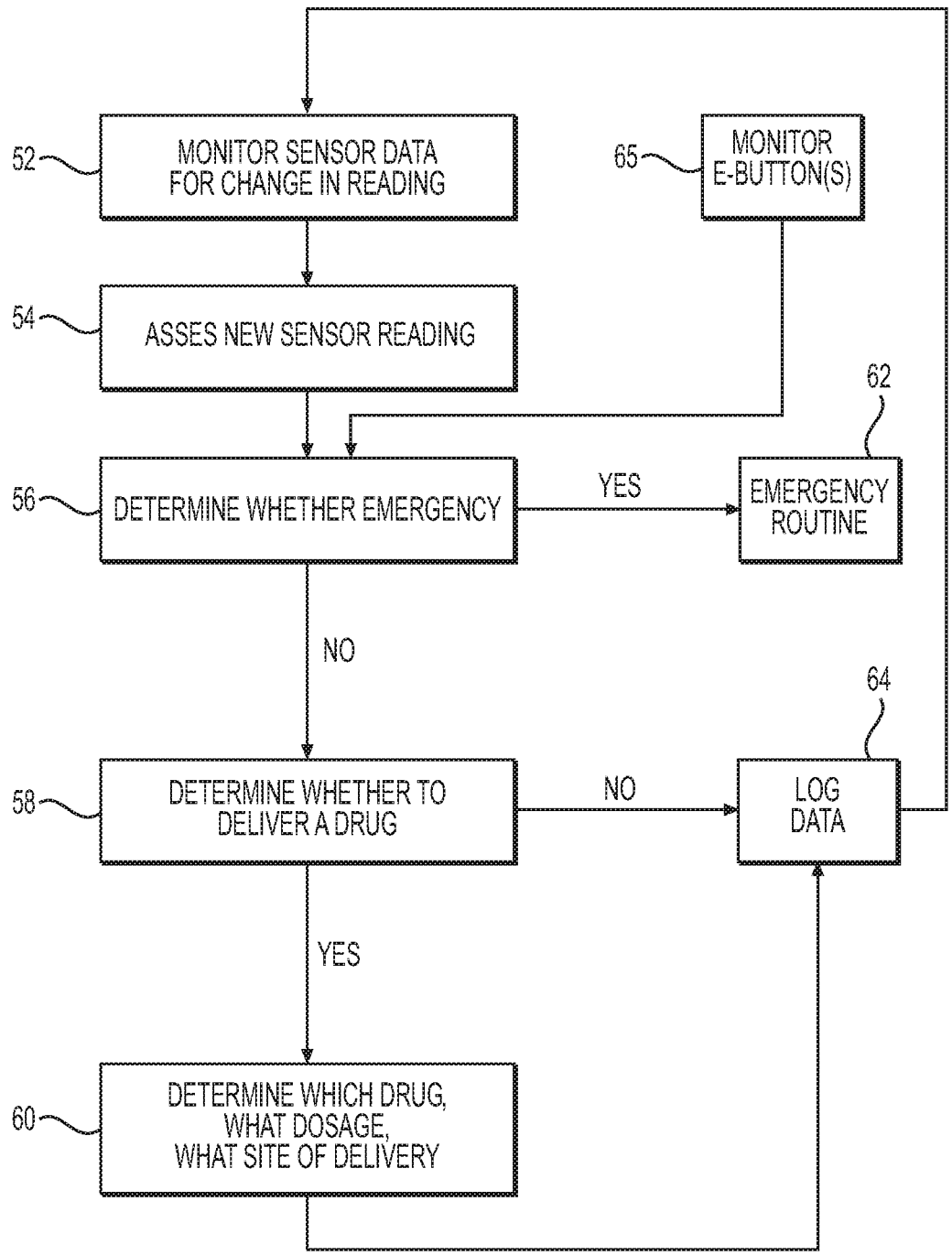
FIG. 5 illustrates a method flow chart of processes in an embodiment of the invention.

FIG. 5 illustrates a typical embodiment of the device functionality in a flowchart form. The embodiment of FIG. 5 illustrates a determination of drug delivery or emergency situations based on sensor and other input. In one example, this particular embodiment would generally be expected to be used by a health care provider or provider team who has programmed a device and prescribed an accompanying transdermal patch to administer a hypertension treatment drug. Here, the pre-programmed values are already in the device, but it is understood in the art that such values may change per configuration of the device in different settings, or with improved values based on research or other information, or in real time by a remote computer connected to the device, e.g., based on updates from the healthcare provider. Further embodiments contemplate that there are no pre-programmed values in the device, and all comparison and determination of an emergency or other situation is conducted by a remote server receiving raw and/or pre-processed instrument data.

Any applicable sensor readings would be monitored by the device 52, e.g., any change of or existence of sensor readings for, if such sensors are available, blood pressure, body temperature, heartrate, other physiological readings or non-physiological readings. In manual configurations, the sensor detection 52 may be replaced by a time or other non-physiological sensors inputs indicating whether administration should occur. The device then assesses the sensor readings 54, meaning that in typical embodiments the device receives the raw data from sensors and by way of example processes it locally to determine the signal from the noise in a readily computer readable format. The computing module would typically perform this function 54 by receiving the data from the sensors and processes the data into a quantitative metric. The pre-programmed values, i.e., data or metrics, would be transferred to the computing module of the device. The computing module compares the processed instrument data with the pre-programmed values as part of the assessment function 54. Based on the comparison, the computing module determines whether an emergency situation exists 56. Based on this determination, the device either engages in an emergency routine which would include typically sending an emergency signal 62, or moves to the next step in the regular control configuration 58. In the emergency routine 62 situation, the cycle may still repeat with a new sensor and measurement thereof, but programming and preset values may be different to reflect the nature of the emergency status or mode. For example, for a diabetic the device may be programmed to be more sensitive to insulin or blood sugar sensor readings, or for other emergency configurations non-essential sensors or components may be shut down so that power could be preserved for wireless communications. In further configurations, sensors may detect an active pharmaceutical ingredient or chemical or drug in the blood, or the concentration in the blood. The chemical detected could be an indicator of the presence of the drug, such as a metabolite or other substance created by the body, or a subpart of the drug, or it may detect the exact same chemical that had been administered as part of the feedback loop. In other embodiments, the administration of a drug may be oral or not part of any automated loop, yet one or more sensors may still be configured to detect it to inform the rest of the loop.

In the flowchart on FIG. 5, the device determines whether to deliver a drug 58. It is noted that although not shown, other medical devices may be activated by the wearable device other than those designed for drug delivery, e.g., a central processing unit may determine to activate an AED and at what particular configuration or setting based on sensor measurements. Certain embodiments of the instant invention are contemplated and may provide for administration of other substances, or even to take medically preferred or indicated actions (such as an AED electrical administration). Such administration by a variety of different administration devices, which may be incorporated into the broader wearable medical device or system, may include saline solution, ringer's solution, fluids, nutraceuticals, and homeopathic formulations to establish and balance homeostasis within a human, patient, or mammalian subject.

Such determination over whether to deliver a drug, a substance, or to take another medically indicated or preferred action such as AED activation is typically made by comparison of processed sensor data to preset data. For example, if sensors indicate to the device that blood pressure is rising, but there is no emergency situation, then the CPU of the device (or a remote server) may determine that it is appropriate to deliver a drug to affect blood pressure. At that time, the next step in the configuration is to determine which drug, what dosage, and what side of delivery 60. The patient may have one or more medical devices connected to the device and capable of administering a drug. Typically, the administration of the drug at a particular dosage will be driven by a direct response to the condition measured by a sensor. For example, if a sensor reads high blood pressure and the device determines a drug administration is needed, then a betablocker may be administered which would be expected to have a direct response on the blood pressure. However, other prophylactic or secondary drugs may also be administered, for example a patient may be understood to be anxious about any perceived increase in blood pressure however small so even though a drug responding directly to the blood pressure sensor measurement may not be administered, an anti-anxiety drug may be administered instead. Transdermal sites of delivery as well as other delivery and medical devices are contemplated in the art. Programming for the determination of which drug is delivered, the dosage, and the medical device utilized 60 is generally done by a medical professional. However, the programming implanting the actual delivery would typically be done by a biomedical engineer, e.g., determining current and voltage signaling patterns appropriate for an electrically operated pump or transdermal patch connected to the device 10. In either case whether the device proceeds with administration or delivery of a drug 58, data is logged 64 on the device, and stored locally and/or remotely. Such logging, storing, and transmission may be performed by a secure ledger system such as block chain. Further, monitoring of emergency buttons 65 either physically located on the device or remotely physically located, or "soft key" virtual emergency buttons are contemplated as providing an input to the CPU or remote server determination of an emergency situation 56.

It is noted that FIG. 5 presents an embodiment of a feedback loop control configuration for a device since after logging data 64 the device returns to its initial state of monitoring sensor data 52. Other control configurations understood by a person of ordinary skill in the art are also contemplated, some of which may or may not overlap with the feedback loop embodiment in FIG. 5. For example, open or closed loop control configurations are contemplated. Typically, a closed loop embodiment would mean that the blood pressure and diagnostic functions of the device (arterial and venous blood flow, respiration, heart beat and pulse, electrocardiograma linked to the drug delivery system to dispense the drug at a controlled rate. If the blood pressure, pulse rate and other indicators go beyond the normal limits of cardiovascular stress leading to a heart attack or stroke, the loop system indicator will alert the patient, and communicate with physician, and emergency room (if the EMS system is required).

The administration of medical care by the device contemplated by FIG. 5, and other such embodiments, may be particularly important as a backup emergency system to administer medical care, since emergency management systems may have significant delays to attend to the patient via ambulance and, especially in rural areas or in the theatre of war, medical attention is commonly unavailable.

During normal daily usage, the device is contemplated to work as an open loop system, monitoring and dosing the patient as required by the physician. In certain embodiments, the amount of drug dosage via the skin and in the blood will be measured via micromachined spectrophotometry to insure dosage of drug delivered. In further embodiments, interactive drug delivery via a transdermal microneedle or transdermal patch is contemplated. A singularity or plurality of the microneedle or transdermal patch can be configured orthogonally to increase the amount of drug permeated thereby improving such administration to levels competitive with a syringe or needle administration of drugs. In addition, certain patches may apply continuous fluid medium from an optional external reservoir via glass or plastic vials of one or more drug solution, but without the use of a hypodermic needle for infusion of a pharmaceutical. Such vials may be connected to tubes to four or more transdermal patches for active or passive transdermal drug delivery. Furthermore, when using the external reservoir, the delivery of drugs transdermally can be regulated and monitored through a computer chip and "pump" administration system interactively via a ledger system such as block chain that records the titration rate, amount and dosage of medication supplied. The pump can vary the speed of introduction of the transdermal permeant at a desired rate.

Generally, an open-loop system is preferred by medical professionals when the drug response to a particular patient is poorly understood or could be susceptible to safety risks. Closed loop systems relying upon feedback are to consider the current output and alter it to the desired condition may be more preferred when dose responses and safety are better understood for the patient in terms of the drug, mode of delivery, dosage, and sensor reliability (including based on prior long term use of the device). Further, if there are less complexities and a more predictable nature about a patient's condition and drug usage, then an open loop may be preferred. A closed loop may more easily account for and react to external disturbances. However, in a closed loop system especially when managing patient welfare it is expected that programmed systems to monitor gain and stability of the control loop would be employed by users and/or providers.

Figure 6:
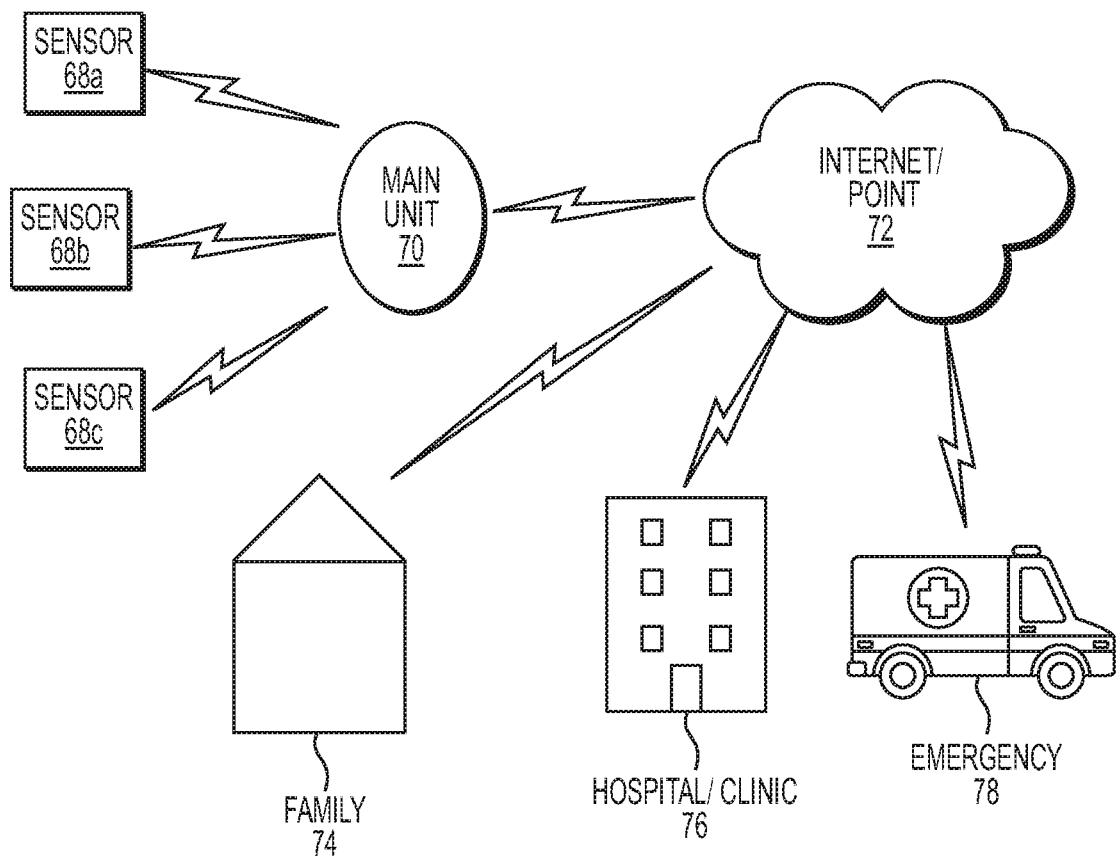
FIG. 6 illustrates a network communication and data transmission embodiment of the invention.

FIG. 6 illustrates an embodiment of a network capable of connecting a plurality of a device 70 receiving data from wired or wireless sensors 68a, 68b, and 68c through typically wireless transmission to the Internet of an access point 72, and through the Internet to remotely located computing devices such as computers or servers at a family home (or family members' smartphones) 74, hospital or clinic 76 which may be a proprietary network, or emergency services 78. It is further contemplated that the devices 70 may be connected to any public network (not only to the Internet or World Wide Web), or such devices 70 may be connected to such public network by means other than through wireless transmission to a cellular tower. For example, other access points to the Internet are contemplated which would subsequently connect the device 70 to a proprietary provider network such as through local Wi-Fi. This may be optimal in situations where the device is being tested in an in-patient unit before the patient is released by medical staff.

In a typical embodiment, the computers 76 on a proprietary network are owned by medical providers or clinics. The devices 70 are in communication with the computers 76 and may transmit sensor data, readouts, device status, or processed information or data. The computers 76 are monitoring the devices 70 at all times when such devices 70 are worn by a patient, and the computers 76 are operating software to detect and respond to emergency signals from the devices 70.

Communication between the device 70 and the hospital servers 76 in FIG. 6 is typified by information related to the sensor measurements on the device 70. In one embodiment, the device 70 may communicate if and when the computing module processes information locally from at least one sensor and determines a high likelihood of an emergency situation (e.g., a degradation or spike of heartrate or blood pressure). Such determination may be the result of comparing sensor data with pre-programmed information or data on the device 70. Or in other embodiments, the computing module of the device 70 may, in addition to a local comparison, transmit its analysis along with pre-processed sensor data. Such processing and/or pre-processing of sensor data is advantageous in an emergency situation because time is critical to the patient, and the signal sent to a proprietary network 76 (or even emergency proprietor network 78) should typically contain only the bare essential information to ensure speed of transmission. When an emergency situation is determined with a high degree of confidence by the device 70 then typically certain sensors 68*a-c* in the device 10 will begin real-time streaming either with raw instrument measurements from important sensors (such as heart-rate and/or blood pressure) or depending on the available bandwidth of the connection, the device 70 will begin real-time streaming pre-processed or roughly or quickly pre-processed data from such instrument measurements. This provides the emergency responders 78 with important real time information to further assess the emergency situation and the patients actions, and permits emergency responders 78 to provide the patient or a caregiver with advice, instructions, or updates. In further embodiments, in such an emergency condition an audio-visual component of the device may transmit to a nearby cell phone (or may be transmitted to an audio-visual component installed into the instant inventions). This will permit health care providers to monitor and be in constant audio-visual contact with the patient in the event of an emergency or reminding the patient to be compliant to treatment protocols. The patient can be seen visually via a monitor from the instant invention for the health care provider to visually diagnose the condition of the patient remotely.

Further, such real-time data capture and transmission, and audio-visual features may be used in other embodiments where healthcare providers and/or an individual or patient may prefer interactive diagnostics. Interactive diagnostics may be used by healthcare providers as a quantitative way of assessing treatment efficacy, for example because accurate and objective measures of symptoms may be assessed through the device 70. Thus, such embodiments may be a valuable tool for clinicians in disease management. Thus, embodiments of the invention may provide for monitoring of patients between outpatient visits. Healthcare providers may also more easily, and in certain cases remotely, change or amend treatment interventions based on the needs of the individual patient.

In still other embodiments of the invention, an embodied system may provide data in clinical studies or other broad health care related data inquiries. For example, the device 70 may transmit sensor 68*a-c* information to the proprietary network 76 which is operated by clinical researchers, private investigators, principal investigators, the NIH, the FDA or other health authorities, or vendors such as a contract research organization. This is an improved system to collect clinical study data that had previously been collected by telephone calls and mailed questionnaires. The collected data is more accurate than that received by patient responses because it is actual recordings from sensors. Moreover, because of reduced costs and labor over telephone calls or mailings, the data may be collected more frequently thereby providing better inputs for subsequent regulatory approvals. The invention may also be used for randomized clinical trials in cases where the proprietary network 76 is gathering information from a large sampling of devices 70. For example, certain individuals having devices 70 could be selected for the randomized trial, and (assuming institutional review board approval) conditions for the automated or remote administration of medical care could be reprogrammed or changed to conduct the study in an experimental set of individuals or patients. Such embodiments may be preferable because they permit more optimal design of experiment or "powering" of clinical studies, i.e., to achieve high quality data with the least amount of experimental subjects. This may be useful for new therapies or treatments depending on the budget of the study, and any risks to patients.

As required, detailed embodiments of the present invention are disclosed herein; however, while various embodiments and examples of this invention have been described above, these descriptions are given for purposes of illustration and explanation, and not limitation. Variations, changes, modifications, and departures from the systems, apparatus and methods disclosed above may be adopted without departure from the spirit and scope of this invention. Moreover, specific structural and functional details disclosed herein are not to be interpreted as limiting, but merely as a basis for the claims and as a representative basis for teaching one skilled in the art to variously employ the present invention. It will be apparent to those skilled in the art that many changes and substitutions may be made to the foregoing description of preferred embodiments and examples without departing from the spirit and scope of the present invention, which is defined by the appended claims.

Further, the purpose of the Abstract is to enable the various patent offices and the public generally, and especially practitioners in the art patients, care providers, healthcare providers, and those who manage or supervise or purchase and/or evaluate technology for or on behalf of the same, but who may not be familiar with patent or legal terms or phraseology, to determine quickly from a cursory inspection the nature and essence of the technical disclosure of the application. The Abstract is not intended to be limiting as to the scope of the invention in any way.

What is claimed is:

1. A medical device worn by an individual previously diagnosed with a blood pressure condition comprising a central processing unit, a memory unit containing programming and diagnostic values, a wireless communications component, at least one sensor capable of measuring diastolic and systolic blood pressure, at least one sensor capable of measuring heartrate, at least one button to transmit an emergency signal to others, and at least one medicament administration device containing at least one active pharmaceutical ingredient;

wherein the central processing unit, the memory unit, and the wireless communications unit are inside a single container removably affixed to a patient;

wherein the central processing unit receives information from, and sends information and instructions to, the memory unit, and wireless communications unit, the sensors, and the at least one medicament administration device;

wherein the central processing unit may instruct the at least one medicament administration device to administer at least one active pharmaceutical ingredient to a patient;

wherein the at least one button to transmit an emergency signal to others, or prevent the administer at least one active pharmaceutical ingredient, is pressed in a certain pattern depending on the individual using it;

wherein the wireless communications component is in frequent communication with remote computers on a propriety healthcare provider network via at least one internet access point; and, wherein the frequent communication(s) contains information about sensor measurements, and central processing unit instructions.

2. The medical device of claim 1 wherein the single container is removably affixed to the patient's body and further comprises an automatic external defibrillator.

3. The medical device of claim 2 wherein the wireless communications component connects to the Internet through either at least one cellular communications tower or at least one Wi-Fi access point.

4. The medical device of claim 3 wherein the central processing unit receives information from, and sends information and instructions to, the sensors by Bluetooth wireless technology.

5. The medical device of claim 4 having at least two sensors capable of measuring diastolic and systolic blood pressure removably affixed to the patient's body.

6. The medical device of claim 5 wherein one blood pressure sensor is removably affixed to one of the patient's arms, and one blood pressure sensor is removably affixed to one of the patient's ankles.

7. The medical device of claim 2 further comprising a global positioning system located inside the container, and which provides location information to the central processing unit.

8. The medical device of claim 1 wherein the at least one active pharmaceutical ingredient is one that is approved by and indicated by the FDA to reduce blood pressure in patients, and wherein the at least one medicament administration device is a transdermal patch.

9. The medical device of claim 8 wherein the at least one active pharmaceutical ingredient is classified as a beta blocker.

10. The medical device of claim 8 wherein the at least one active pharmaceutical ingredient is classified as a central-acting agent.

11. The medical device of claim 10 further comprising two sensors capable of measuring diastolic and systolic blood pressure wherein:

there is only one medicament administration device that is a transdermal patch removably affixed to the patient's skin under a garment;

there is only one active pharmaceutical ingredient that is clonidine;

the central processing unit may instruct the medicament administration device to administer clonidine based on the two blood pressure sensor measurements, and the at least one heartrate sensor measurement.

12. The medical device of claim 11 wherein the central processing unit instructions, the blood pressure sensors and heartrate sensor(s) measurements, and the administration of clonidine comprise a closed feedback control loop further comprising an emergency routine exit point to the loop.

13. The medical device of claim 8 wherein the at least one active pharmaceutical ingredient is classified as a vasodilator.

14. A method for monitoring a patient's blood pressure and administering a drug in a closed feedback control loop comprising: a central processing unit receiving wireless information about blood pressure from at least one blood pressure sensor that is removably affixed to a patient's body, and receiving wireless information about heartrate from at least one heartrate sensor that is removably affixed to a patient's body; processing the received information in a central processing unit; determining whether an emergency condition exists by comparing the processed information to pre-programmed values in the central processing unit; if there is an emergency condition, activating an emergency routine requiring wirelessly communicating with a healthcare provider; if there is no emergency condition, determining whether to administer a drug based on an administration evaluation program in the central processing unit; if an emergency is felt and/or an individual needs assistance, then a button may be pressed in a certain pattern depending on the individual using it; if the patient does not to want to administer a drug based on an administration evaluation program in the central processing unit, then pressing the button in the certain pattern or a different certain pattern; if a drug is determined to be administered, determining a dosage of the drug and from which application device to administer it, and sending a set of instructions containing dosage information to a medicament application device located on or near the patient's body.

15. The method of claim 14 wherein the emergency routine comprises communicating with a pre-determined health care provider, communicating with a city or county emergency service provider, and communicating with at least one family member's mobile telephone via text message and pre-recorded voice call.

16. The method of claim 15 wherein the emergency routine further comprises communicating blood pressure and heartrate sensor information in real time with emergency service providers over the Internet.

17. The method of claim 15 wherein the central processing unit is sending the set of instructions via a wired system to the medicament application device, and wherein the medicament application device is programmed to confirm the fidelity of the set of instructions.

18. The method of claim 17 wherein the drug is an FDA approved drug indicated for hypertension and is selected from the class of beta blockers, central-acting agents, and vasodilators.

19. A medical system worn by an individual comprising a central processing unit, a memory unit containing programming and diagnostic values, a global positioning system unit, a wireless communications component, at least one sensor capable of measuring diastolic and systolic blood pressure, at least one sensor capable of measuring blood sugar, at least one sensor capable of measuring heartrate, at least one sensor capable of measuring an active pharmaceutical ingredient in the blood, at least one button that contacts emergency services and/or family member(s), and at least one medicament administration device containing at least one active pharmaceutical ingredient;

wherein the central processing unit, the memory unit, the global positioning system unit, and the wireless communications unit are inside a single container removably affixed to a patient;

wherein the central processing unit receives information from, and sends information and instructions to, the memory unit, and wireless communications unit, the sensors, and the at least one medicament administration device in a closed feedback control loop further having an emergency routine exit in the loop;

wherein the wireless communications component is in constant communication with remote computers on a propriety healthcare provider network via at least one internet access point;

wherein the frequent communication(s) contains information about sensor measurements, location information from the global positioning system unit, and central processing unit instructions;

wherein the central processing unit may instruct the at least one medicament administration device to administer to a patient one or more active pharmaceutical ingredient(s), such as beta blockers, central-acting agents, vasodilators, alpha blockers, alpha-beta blockers, aldosterone antagonists, and renin inhibitors, and/or substances FDA approved for the treatment of insulin;

wherein the at least one button may be pressed in a certain pattern to call for help and another pattern to stop emergency help.

* * * * *